(12) United States Patent
Hucker et al.

(10) Patent No.: US 9,829,450 B2
(45) Date of Patent: Nov. 28, 2017

(54) STRUCTURAL HEALTH MONITORING

(71) Applicant: BAE Systems plc, London (GB)

(72) Inventors: Martyn John Hucker, South Gloucestershire (GB); David William Gough, South Gloucestershire (GB)

(73) Assignee: BAE Systems plc, London (GB)

( * ) Notice: Subject to any disclaimer, the term of this patent is extended or adjusted under 35 U.S.C. 154(b) by 0 days.

(21) Appl. No.: 15/312,684

(22) PCT Filed: Feb. 5, 2015

(86) PCT No.: PCT/GB2015/050318
§ 371 (c)(1),
(2) Date: Nov. 21, 2016

(87) PCT Pub. No.: WO2015/181516
PCT Pub. Date: Dec. 3, 2015

(65) Prior Publication Data
US 2017/0184525 A1    Jun. 29, 2017

(30) Foreign Application Priority Data

May 28, 2014  (EP) ..................................... 14275129
May 28, 2014  (GB) .................................. 1409430.4

(51) Int. Cl.
G01N 25/72       (2006.01)
B29C 70/88       (2006.01)
(Continued)

(52) U.S. Cl.
CPC ........... *G01N 25/72* (2013.01); *B29C 70/885* (2013.01); *G01N 25/18* (2013.01); *G01N 27/20* (2013.01);
(Continued)

(58) Field of Classification Search
USPC ............................................ 374/45, 57, 4, 5
See application file for complete search history.

(56) References Cited

U.S. PATENT DOCUMENTS

| 6,595,584 B1 | 7/2003 | Casagrande |
| 8,393,784 B2 | 3/2013 | Ringermacher |
| 2001/0005392 A1 | 6/2001 | Schultz |

FOREIGN PATENT DOCUMENTS

| GB | 2421952 A1 | 7/2006 |
| WO | 2004065926 A1 | 8/2004 |

OTHER PUBLICATIONS

International Preliminary Report on Patentability for Appl No. PCT/GB2015/050318 dated Nov. 29, 2016, 8 pages.
(Continued)

*Primary Examiner* — Mirellys Jagan
(74) *Attorney, Agent, or Firm* — Maine Cernota & Rardin

(57) ABSTRACT

The invention relates to improved structural health monitoring, particularly to structural health monitoring of fiber reinforced polymer composites, more particularly at bonded joints and methods thereof. There is provided a method of structural health monitoring a composite structure (12), wherein said structure (12) comprises at least one non-reinforcing thermal element (18), such as electrically conductive fibers, comprising the steps of applying a stimulus to cause heating of said thermal element (18), removing the stimulus, and measuring the electrical resistance of said element (18) as a function of time, to provide a thermal decay profile (41, 42) indicating whether damage has occurred in the composite structure (12).

15 Claims, 2 Drawing Sheets

(51) Int. Cl.
*G01N 25/18* (2006.01)
*G01N 27/20* (2006.01)
*G01N 33/44* (2006.01)
B29C 37/00 (2006.01)
G01N 27/04 (2006.01)

(52) U.S. Cl.
CPC ........ *G01N 33/442* (2013.01); *B29C 2037/90* (2013.01); *G01N 27/04* (2013.01)

(56) References Cited

OTHER PUBLICATIONS

European Search Report for Appl No. 14275129.6 dated Dec. 4, 2014, 8 pages.
Great Britain Search Report for Appl No. 1409430.4 dated Oct. 29, 2014, 4 pages.
International Search Report for Appl No. PCT/GB2015/050318 dated Mar. 30, 2015, 13 pages.
Shoukai Wang et al: "Self-sensing attained in carbon-fiber-polymer-matrix structural composites by using the interlaminar interface as a sensor", Smart Materials and Structures, IOP Publishing Ltd., Bristol GB, vol. 13, No. 3, Jun. 1, 2004, ISSN: 0964-1726, DOI: 10.1088/0964-1726/13/3/017.

STRUCTURAL HEALTH MONITORING

The invention relates to structural health monitoring, particularly to structural health monitoring of fibre reinforced polymer composites, more particularly at bonded joints and methods thereof.

Composite materials are widely used and are replacing metals, alloys as structural or construction materials. Composite materials are prone to delamination and failure at bonded joints. It is desirable to be able to continuously monitor the structural health of the composite rather than allow a serious defect and catastrophic failure to occur.

According to a first aspect of the invention there is provided a method of structural health monitoring a composite structure, wherein said structure comprises at least one non-reinforcing thermal element, wherein the thermal element is electrically isolated from the fibre plys, comprising the steps of applying a stimulus to cause heating of said thermal element, removing the stimulus, and measuring the electrical resistance of said element as a function of time, to provide a thermal decay profile of the thermal element.

The thermal decay profile may be monitored and compared to a library of reference thermal decay profiles, such that the structural health of the composite may be readily compared to reference materials, and reference failure modes, to determine any patterns that may lead to a failure, such as, for example delamination or debonding.

The composite structure may comprise a binder matrix comprising fibre reinforcement. The fibre reinforcement may be fibres, or woven fibre plys. The fibre reinforcement may be glass, polymer, ceramic or textiles, and may be selected depending on the desired mechanical or physical properties of the composite; the fibre reinforcement may be such as for example glass, carbon fibre and silicon carbide. The binder matrix may be a resin or ceramic binder matrix, preferably a resin binder, such as for example an epoxy resin.

The thermal element may be a conductive fibre, metal wires, foils, printed conductive inks, conductive polymers or deposed conductive composition, preferably at least one electrically and thermally conductive fibres conductive tow. The thermal element may comprise a metalloid, such as a metal, alloy or semiconductor. The thermal element may take the form of a wire, or fibre.

The electrically conductive fibres may include carbon fibres and/or electrically non-conductive fibres with a conductive coating. Examples of electrically non-conductive fibres include glass fibres, polymer fibres, ceramic fibres such as silicon carbide fibres, and textile fibres. Examples of textile fibres include natural fibres such as cotton and synthetic fibres which are typically polymer fibres such as Nylon® and polyester.

The thermal element is a discrete non-load bearing, non-reinforcing thermal element, hence provides no structural reinforcement of the laminate or bonded laminates. The non-reinforcing thermal element may be located or applied to a reinforcing fibre ply. The non-reinforcing thermal element may be electrically and thermally insulated from said reinforcing ply.

The thermal element may be arranged or deposed in a pattern or motif to provide optimal coverage of the area or region to be monitored.

The thermal element may electrically isolated from the fibre plys and any other thermal elements that may be present. The thermal element and detector element may be separated from a fibre ply by means of a barrier, such as for example a deposed layer of an electrically non-conductive material, where the fibre ply is non electrically conductive an electrically non-conductive barrier may not be required. In a preferred arrangement the barrier may have thermal insulative properties. The barrier may simply be a portion of binder matrix. The arrangement or deposition of the thermal element and/or detector element on or substantially on a fibre ply, allows for the element to be supported during the layup and curing processes.

The thermal coefficient of resistivity effects precludes the use of the reinforcing fibre ply sheet as the thermal element. The current distribution across large interlaminar areas and thickness variations would reduce the ability to localise the data.

According to a further aspect of the invention there is provided a composite material comprising at least one fibre ply, at least one non-reinforcing thermal element wherein said thermal element is electrically isolated from the at least one fibre ply, wherein said thermal element and at least one fibre ply are encapsulated in a cured resin binder matrix.

In a preferred arrangement the composite further comprises a detector element, wherein said detector element is electrically isolated from the at least one fibre ply and the at least one thermal element.

In a further arrangement a detector element may be located proximate to the thermal element, and thus measuring the electrical resistance of said detector element as a function of time, may provide a detector element thermal decay profile. The detector element thermal decay profile may then be compared to a library of reference detector element thermal decay profiles, such that the structural health of the composite may be readily compared to reference materials, and reference failure modes, to determine any patterns that may lead to a failure, such as, for example delamination or debonding.

The thermal decay profiles of the thermal element and/or detector elements will change when the physical or chemical properties of the composite change. The thermal decay profiles are affected by the resistivity of the thermal and/or detector elements, and the loss of the heat from the element by conduction/radiation in its immediate environment. Therefore provided that the heating profile of the thermal element is kept constant, same rates of heating are applied, any change in the decay profile may be attributed to changes in the environment surrounding the thermal and/or detector element, such that any cracks, delamination, debonding will alter the rate of heat loss from the thermal element and hence the thermal decay profile of the thermal and or detector elements, when compared to reference materials or when compared to the actual composite material when it was first manufactured, such that any changes in the thermal decay profile may be detected without removal of the composite and effectively monitored "in-situ", without the need for detectors or sensors external to the laminate. This allows the effective monitoring of the structural health of a composite in real time.

The heating profile may be dictated by the thermal properties of the composite structure, such as for example, dimensions, geometry, mass, thermal conductivity, heat capacity.

The structural health monitoring may be observed over substantially all of a composite structure or at points of high stress or strain or known failure points. Typical microstructure damage in composites may comprise matrix cracking, fibre-matrix debonding, fibre failures and fibre pull-out, these may all have an impact on the thermal transport within the composite due to increased interfacial scattering and by creation of longer effective thermal path lengths.

In a preferred arrangement said thermal element and said detector element are located either side of a bonded joint line of a composite, preferably directly opposite i.e. coplanar, with respect to each other in the bondline. For example wherein the composite is formed from a first composite body fixedly attached to a second composite body, by a bonded joint, wherein the first composite body comprises at least one thermal element, the second composite body comprises at least one detector element, such that said thermal and detector elements are located either side of the bonded joint. This allows the effective structural health monitoring of the bonded joint, which joins the first and second composite bodies to form a joined composite. The bonded joints are a common failure point, and so in-situ monitoring provides useful real time structural health monitoring of the bonded joint.

According to a yet further aspect of the invention there is provided a structural health monitoring system for monitoring a composite comprising a composite as defined hereinbefore, comprising a power source to resistively heat the thermal element, and at least one sensor for recording the change in resistance as a function of time for the thermal and/or detector element.

A composite according to the invention may conveniently be made by any known composite manufacturing processes, such as for example, wet layup; pre-pregging; resin infusion or resin transfer moulding or vacuum assisted resin transfer moulding may all be used. Use of such well known techniques allows great flexibility in form and size of the composite thus formed. One advantage of using these commonly used techniques is that composites of the invention may be employed to replace already existing parts made by the same techniques but not having the advantage of having structural health monitoring formed integral therewith.

Composites according to the invention may be used in new designs or to replace worn, damaged or outdated parts of any items which can be manufactured of composite material. For example, vehicles, whether land, air, space or water born, may have parts manufactured with integral SHM (structural health monitoring), according to the invention. Examples of such use may include wing skins on aircraft, and in particular unmanned air vehicles, where composites according to the invention may be used to monitor SHM.

Further potential uses on vehicles may include body panels on hybrid or electric drive vehicles where the composites of the invention can be used to save weight and bulk, compared to conventional SHM techniques. Such composites may also find use on free flooding hydrodynamic hulls of, say, submersible remotely operated vehicles. The composites would be especially useful on any vehicle where weight or bulk was at a premium like an aircraft or a satellite.

In buildings, composites according to the invention may comprise wall panels in portable or temporary buildings, room dividers, suspended ceiling panels, doors or window frames. Any composite used in a construction of a body, such as, for example a structure, vehicle, vessel or craft will undergo certain stresses and strains during its working life and may be subject to material fatigue, hence in-situ real time monitoring and which may be monitored remotely will provide guidance on the structural health of the body, to ensure structural integrity of said body.

The thermal decay may be measured using constant/fixed temperature control rather than fixed voltage/time. This may use feedback from the driven thermal element in a similar manner to a constant temperature anemometer circuit in order to bring it to the same temperature before each reading and so may provide a more stable/repeatable baseline.

In a further arrangement to cyclic sampling regime may be used to sweep the thermal element temperature between two pre-set limits. On the cooling segments the temperature would either be allowed to drop at the natural rate or may be driven at a reduced rate to give a retarded reduction in temperature. The heat input pulse to rest time ratio will depend on how the time taken for the composite structure proximate to the thermal elements can cool.

Whilst the invention has been described above, it extends to any inventive combination of the features set out above, or in the following description, drawings or claims.

Exemplary embodiments of the device in accordance with the invention will now be described with reference to the accompanying drawings in which.

Figure 1:
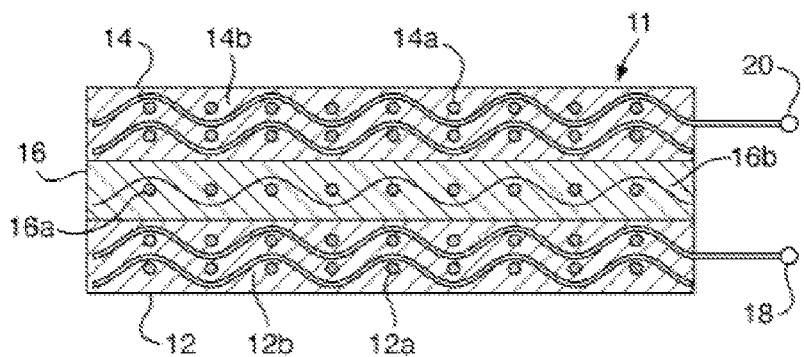
FIG. 1 shows a cross sectional side view of a composite with integral SHM, according to the invention.

FIG. 1 shows an example of a composite, depicted generally at 11, comprising a first composite structure 12 which is bonded via bonded joint 16 to a second composite structure 14. The first and second composites 12, 14 contain a thermal element 18 and a detector element 20. The thermal element 18 is resistively heated under a controlled rate and when the heating is stopped the thermal decay profile of the thermal element 18 and detector element 20 is monitored and recorded as a function of time.

Each of the first and second composites 12, 14 are formed as a composite material comprising suitable fibre plys 12b and 14b in a binder matrix. The composites may also comprise filler materials 12a, 14a in respective binder matrices 12b, 14b. The bonded joint 16 may also comprise at least one fibre ply 16b and optional filler materials 16a, in a binder matrix to promote adhesion, between said first and second composites 12 and 14.

The composite of the invention can be manufactured in different ways. For example, it is possible to fully manufacture each of the first and second composite structures and then bond the two together via a bonded joint. Alternatively, each structure may be produced separately, but with partial cure of the binder matrices, so that the structures can be co-cured together. The entire structure may be formed with a common binder matrix, for example in a wet lay up process, to provide a 'monolithic' structure for the component.

Figure 2:
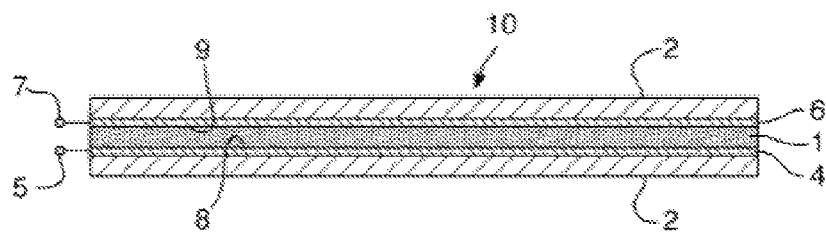
FIG. 2 shows a cross sectional side view of composite with integral SHM, according to the invention.

FIG. 2 shows a simplified composite 10, formed from a fibre ply 1, with a thermal element 6 laid up on the upper surface of fibre ply 1, separated by a barrier 9. On the lower surface of fibre ply 1 is a detector element 4, separated by a barrier 8. The thermal element 6, detector element 4 and fibre ply 1, are encapsulated in a resin binder matrix 2. The thermal element is resistively heated and the thermal decay profile measured by a control system (not shown) attached via connector 7. The thermal decay profile of the detector element 4 is measured by a control system, may be the same system as for the thermal element, and is connected via connector 5.

Figure 3:
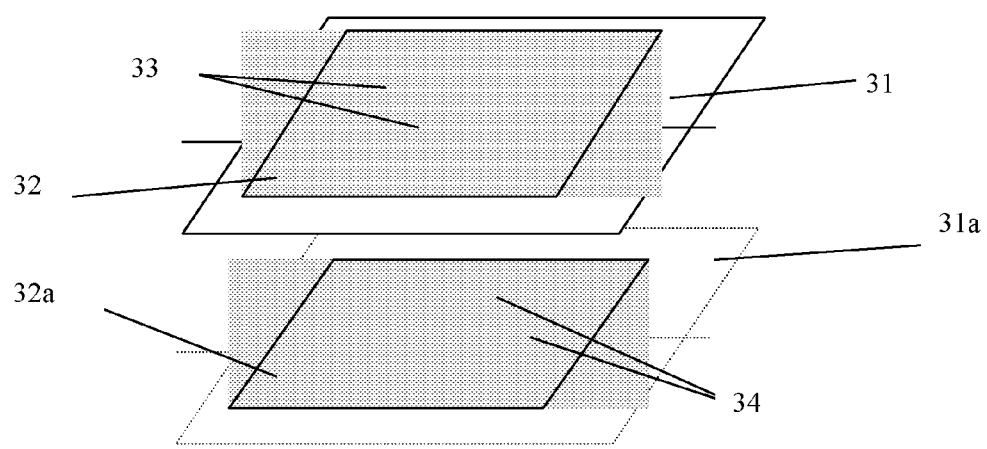
FIG. 3 shows two fibre plys with a thermal and detector element located thereon.

FIG. 3 shows a top view of a fibre ply 31 31a, deposed thereon a separator barrier layer 32, 32a, and deposed on the barrier layer a thermal element 33 and detector element 34.

The deposition may be by deposition techniques such as printing, either direct deposition or using mask or off-set printing techniques.

Figure 4:
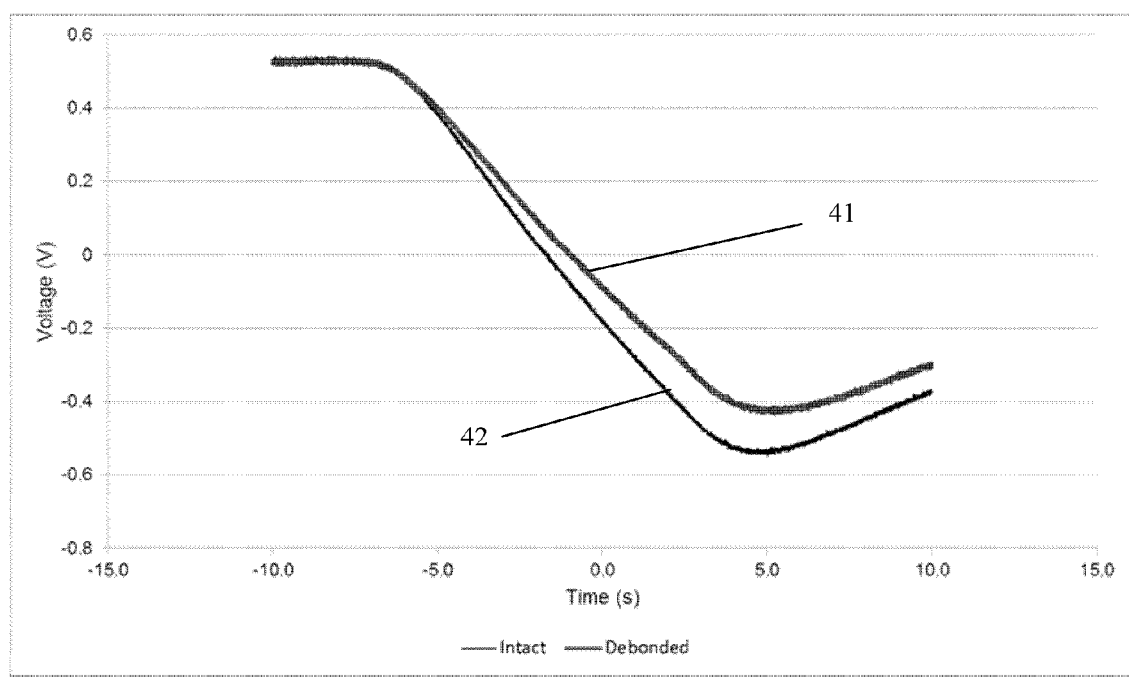
FIG. 4 shows a graph of the voltage vs time plot for a bonded and debonded laminate structure.

FIG. 4 shows a graph of a voltage (y axis) vs. time (x axis) plot, for the change in voltage of a thermal element (as shown) embedded into a debonded (failing) laminate 41, and an intact laminate 42. The input pulse was applied in the range of 1-10 s, and measured (thermal decay 41, 42) responses, as a shown, were recorded over the first 0.1-10 s The plot shows the behaviour of back-to-back bonded strips (~250 mm long) before and after a ~20 mm debonded region was introduced. The debonded sample 41 responds to the heat pulse more slowly due to the changes in the heat path.

The invention claimed is:

1. A method of structural health monitoring of a bonded joint in a composite structure, wherein said composite structure comprises a plurality of fibre plys in a binder matrix, wherein said structure comprises at least one non-reinforcing thermal element, wherein the thermal element is electrically isolated from the fibre plys, the method comprising:
    applying a stimulus to cause heating of said thermal element, wherein the stimulus is resistive heating;
    removing the stimulus;
    measuring a thermal element decay profile, said thermal element decay profile being a change of electrical resistance of said thermal element as a function of time; and
    monitoring the thermal element decay profile and comparing it to a library of reference thermal element decay profiles.

2. The method according to claim 1, wherein the thermal element is deposed in a pattern or motif.

3. The method according to claim 1, wherein the thermal element is at least one electrically and thermally conductive tow.

4. The method according to claim 3, wherein the thermally conductive tow is carbon fibre or metal wire.

5. The method according to claim 1, wherein the composite structure comprises a first composite body fixedly attached to a second composite body by the bonded joint.

6. The method of claim 5, wherein said thermal element is located in the first composite body and a detector element is located in the second composite body, such that the thermal and detector elements are located either side of a bonded joint line.

7. The method according to claim 1, wherein said structure further comprises a detector element located proximate to the thermal element, and the method further comprises measuring a detector element thermal decay profile, said detector element thermal decay profile being an electrical resistance of said detector element as a function of time.

8. The method according to claim 7, further comprising comparing the detector element thermal decay profile to a library of reference detector element thermal decay profiles.

9. The method according to claim 7, wherein said structure further includes a bonded joint line, and said thermal element and said detector element are located on either side of said bonded joint line.

10. A method of structural health monitoring of a bonded joint in a composite structure, wherein said composite structure comprises a plurality of fibre plys in a binder matrix, wherein said structure comprises at least one non-reinforcing thermal element, wherein the thermal element is electrically isolated from the fibre plys, wherein said structure further comprises a bonded joint line and a detector element located proximate to the thermal element, said thermal element and said detector element being located on either side of said bonded joint line the method comprising:
    applying a stimulus to cause heating of said thermal element, wherein the stimulus is resistive heating;
    removing the stimulus;
    measuring a thermal element decay profile, said thermal element decay profile being a change of electrical resistance of said thermal element as a function of time; and
    measuring a detector element thermal decay profile, said detector element thermal decay profile being an electrical resistance of said detector element as a function of time.

11. The method according to claim 10, wherein the thermal element is at least one electrically and thermally conductive tow.

12. The method according to claim 11, wherein the thermally conductive tow is carbon fibre or metal wire.

13. A method of structural health monitoring of a bonded joint in a composite structure, wherein said composite structure comprises a plurality of fibre plys in a binder matrix, wherein the composite structure comprises a first composite body fixedly attached to a second composite body by the bonded joint, wherein said structure comprises at least one non-reinforcing thermal element located in the first composite body and a detector element located in the second composite body, such that the thermal and detector elements are located either side of a bonded joint line, wherein the thermal element is electrically isolated from the fibre plys, the method comprising:
    applying a stimulus to cause heating of said thermal element, wherein the stimulus is resistive heating;
    removing the stimulus;
    measuring a thermal element decay profile, said thermal element decay profile being a change of electrical resistance of said thermal element as a function of time.

14. The method according to claim 13, wherein the thermal element is at least one electrically and thermally conductive tow.

15. The method according to claim 14, wherein the thermally conductive tow is carbon fibre or metal wire.

* * * * *